United States Patent [19]

Haga et al.

[11] Patent Number: 4,670,042
[45] Date of Patent: Jun. 2, 1987

[54] TETRAHYDROPHTHALIMIDES, AND THEIR PRODUCTION AND USE AS HERBICIDES

[75] Inventors: Toru Haga, Takarazuka; Eiki Nagano, Nishinomiya; Ryo Sato; Kouichi Morita, both of Toyonaka, all of Japan

[73] Assignee: Sumitomo Chemical Company, Limited, Osaka, Japan

[21] Appl. No.: 783,104

[22] Filed: Oct. 2, 1985

[30] Foreign Application Priority Data

Oct. 3, 1984 [JP] Japan .................. 59-207498

[51] Int. Cl.⁴ .................................. A01N 43/48
[52] U.S. Cl. ...................... 71/92; 544/354; 548/416
[58] Field of Search .................... 544/354; 71/92

[56] References Cited

U.S. PATENT DOCUMENTS 4,258,185 3/1981 Nakao et al. ................... 544/114

FOREIGN PATENT DOCUMENTS 0077938 10/1982 European Pat. Off. .
0118982 1/1984 European Pat. Off. .

OTHER PUBLICATIONS

Mitsubishi Chem. Abstracts, vol. 94, No. 7, (1981), 94:42637j.
Wakabayashi Chem. Abstracts, vol. 90, No. 1, (1979), 90:6245p.
Wakabayashi Chem. Abstracts, vol. 94, No. 17, (1981), 94:133973g.
Kurasawa Chem. Abstracts, vol. 101, No. 7, (1984), 101:55057h.
Tyblewski Chem. Abstracts, vo. 90, No. 22, (1979), 90:170149f.

*Primary Examiner*—Mark L. Berch
*Attorney, Agent, or Firm*—Birch, Stewart, Kolasch & Birch

[57] ABSTRACT

A compound of the formula:

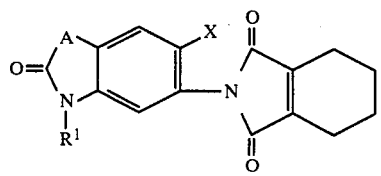

wherein $R^1$ is a $C_1$-$C_5$ alkyl group, a $C_3$-$C_5$ alkenyl group, a $C_3$-$C_5$ alkynyl group or a $C_1$-$C_3$ alkoxymethyl group, X is a hydrogen atom, a fluorine atom or a chlorine atom and A is a group of the formula:

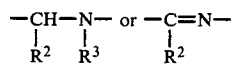

in which $R^2$ is a hydrogen atom or a methyl group, $R^3$ is a hydrogen atom or a methyl group and the nitrogen atom is bonded to the benzene ring, which is useful as a herbicide.

12 Claims, No Drawings

TETRAHYDROPHTHALIMIDES, AND THEIR PRODUCTION AND USE AS HERBICIDES

This invention relates to tetrahydrophthalimides, and their production and use. More particularly, it relates to tetrahydrophthalimides of the formula:

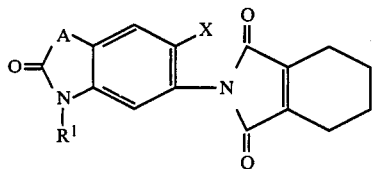

wherein $R^1$ is a $C_1$–$C_5$ alkyl group, a $C_3$–$C_5$ alkenyl group, a $C_3$–$C_5$ alkynyl group or a $C_1$–$C_3$ alkoxymethyl group, X is a hydrogen atom, a fluorine atom or a chlorine atom and A is a group of the formula:

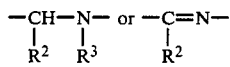

in which $R^2$ is a hydrogen atom or a methyl group, $R_3$ is a hydrogen atom or a methyl group and the nitrogen atom is bonded to the benzene ring, and their production and use.

It has been found that the tetrahydrophthalimides (I) show a high herbicidal activity against a wide variety of weeds including broad-leaved weeds, Graminaceous weeds, Commelinaceous weeds and Cyperaceous weeds in agricultural plowed field by foliar or soil treatment without producing any material phytotoxicity on various agricultural crops such as corn, wheat, rice, soybean or cotton. Examples of broad-leaved weeds are wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), henbit (*Lamium amplexicaure*) jimsonweed (*Datura stramonium*), black nightshade (*Solanum nigrum*), persian speedwell (*Veronica persica*), common cocklebur (*Xanthium pensylvanicum*), common sunflower (*Helianthus annuus*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), etc. Examples of Commelinaceous weeds are asiatic dayflower (*Commelina communis*), etc. Examples of Cyperaceous weeds are yellow nutsedge (*Cyperus esculentus*), etc.

Further, the tetrahydrophthalimides (I) of the invention are effective in exterminating the paddy field weeds including Graminaceous weeds such as barnyardgrass (*Echinochloa oryzicola*), broad-leaved weed such as common falsepimpernel (*Lindernia procumbens*), indian toothcup (*Rotala indica*) and waterwort (*Elatine triandra*), Cyperaceous weeds such as hardstem bulrush (*Scirpus juncoides*) and needle spikerush (*Eleocharis acicularis*) and others such as monochoria (*Monochoria vaginalis*) and arrowhead (*Sagittaria pygmaea*), without any phytotoxicity to rice plants on flooding treatment.

Among the tetrahydrophthalimides (I), preferred are those wherein X is a fluorine atom, particularly those wherein A is $-CH_2-NH-$ or $-CH=N-$, more particularly those wherein $R^1$ is $-CH_2C\equiv CH$ or $-CH_2CH=CH_2$. Specific examples are 2-[1-(2-propenyl)-2(1H)-quinoxalinon-7-yl]-4,5,6,7-tetrahydro-2H-isoindole-1,3-dione, 2-[3,4-dihydro-1-(2-propynyl)-2(1H)-quinoxalinon-7-yl]-4,5,6,7-tetrahydro-2H-isoindole-1,3-dione, 2-[6-fluoro-1-(2-propenyl)-2(1H)-quinoxalinon-7-yl-4,5,6,7-tetrahydro-2H-isoindole-1,3-dione, 2-[3,4-dihydro-6-fluoro-1-(2-propynyl)-2(1H)-quinoxalinon-7-yl]-4,5,6,7-tetrahydro-2H-isoindole-1,3-dione, etc.

The tetrahydrophthalimides (I) of the invention are obtainable by reacting a quinoxaline of the formula:

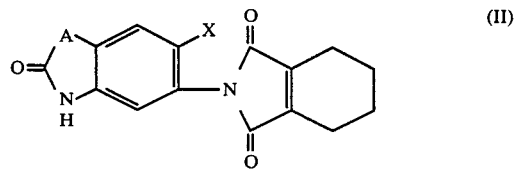

wherein X and A are each as defined above with a halide of the formula:

wherein $R^1$ is as defined above and Y is a chlorine atom, a bromine atom or an iodine atom in a solvent in the presence of a dehydrohalogenating agent at a temperature of 0° to 50° C. for a period of 0.5 to 24 hours.

In the reaction, the halide (III) and the dehydrohalogenating agent are used respectively in an amount of 1 to 3 equivalents to 1 equivalent of the quinoxaline (II). Examples of the solvent are ethers (e.g. diethyl ether, diisopropyl ether, dioxane, tetrahydrofuran, ethylene glycol dimethyl ether), acid amides (e.g. formamide, N,N-dimethylformamide, N,N-dimethylacetamide), sulfur compounds (e.g. dimethylsulfoxide), and their mixtures. As the dehydrohalogenating agent, there may be used inorganic bases (e.g. sodium hydride), organic lithium compounds (e.g. n-butyl lithium, methyl lithium, lithium diisopropylamide), etc.

After completion of the reaction, the reaction mixture is subjected to ordinary post-treatment such as extraction with an organic solvent and concentration. If desired, any conventional purification procedure such as recrystallization or chromatography may be adopted.

Practical and presently preferred embodiments for production of the tetrahydrophthalimides (I) are illustratively shown in the following Examples.

EXAMPLE 1

Sodium hydride (33 mg) was suspended in N,N-dimethylformamide (1.5 ml), and the resultant suspension was cooled to −30° C. 2-(3,4-Dihydro-6-fluoro-2(1H)-quinoxalin-7-yl)-4,5,6,7-tetrahydro-2H-isoindole-1,3-dione (400 mg) was added thereto at −30° C., followed by stirring for 30 minutes. 1-Bromo-2-propyne (165 mg) was added thereto at −30° C., and the temperature was gradually raised to room temperature (e.g.20°-25° C.), followed by stirring for 6 hours. The reaction mixture was admixed with water and extracted with ethyl acetate. The extract was washed with water, dried and concentrated. The residue was purified by silica gel thin layer chromatography using a mixture of ethyl acetate and hexane (1:2) as an eluent to give 2-[3,4-dihydro-6-fluoro-1-(2-propynyl)-2(1H)-quinoxalinon-7-yl]-4,5,6,7-tetrahydro-2H-isoindole-1,3-dione (80 mg). m.p., 205.6° C.

In the same manner as above, the tetrahydrophthalimides (I) as shown in Table 1 can be obtained.

TABLE 1

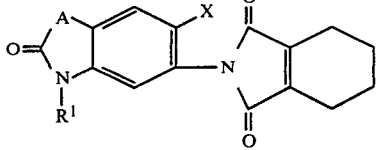
(I)

| Compound No. | X | A | $R^1$ | Physical constant |
|---|---|---|---|---|
| 1 | H | —CH=N— | CH2CH2CH3 | glassy |
| 2 | H | —CH=N— | CH2CH=CH2 | m.p., 170–171° C. |
| 3 | H | —CH=N— | CH2OCH2CH3 | m.p., 162–163° C. |
| 4 | H | —CH=N— | CH2CH2OCH2CH3 | glassy |
| 5 | H | —CH2—NH— | CH2C≡CH | m.p., 199–200° C. |
| 6 | H | —CH2—N(CH3)— | CH2C≡CH | m.p., 164–167° C. |
| 7 | F | —CH2—NH— | CH3 | m.p., 236° C. |
| 8 | F | —CH2—NH— | CH2CH3 | m.p., 193° C. |
| 9 | F | —CH=N— | CH2CH3 | glassy |
| 10 | F | —CH2—NH— | CH2CH2CH3 | m.p., 188–188.6° C. |
| 11 | F | —CH—N(CH3)— | CH2C≡CH | m.p., 152–154° C. |
| 12 | F | —CH2—NH— | CH2CH2CH2CH3 | m.p., 181–181.2° C. |
| 13 | F | —CH=N— | CH2CH=CH2 | m.p., 170.3° C. |
| 14 | F | —CH2—NH— | CH2C≡CH | m.p., 205.6° C. |
| 15 | H | —CH=N— | CH2CH2CH3CH3 | m.p., 110–110.7° C. |
| 16 | F | —CH—NH—(CH3) | CH2C≡CH | m.p., 203.2° C. |
| 17 | Cl | —CH2—NH— | CH2C≡CH | m.p., 214–216° C. |
| 18 | H | —CH=N— | CH2C≡CH | |
| 19 | H | —CH2—NH— | CH2CH=CH2 | |
| 20 | F | —CH=N— | CH2C≡CH | |
| 21 | F | —CH2—NH— | CH2CH=CH2 | |
| 22 | H | —CH=N— | CH2CH3 | |
| 23 | H | —CH2—NH— | CH2CH3 | |
| 24 | H | —CH2—NH— | CH2CH2CH3 | |
| 25 | F | —CH=N— | CH2CH2CH3 | |

The production of the starting quinoxaline (II) is summarized in the following scheme:

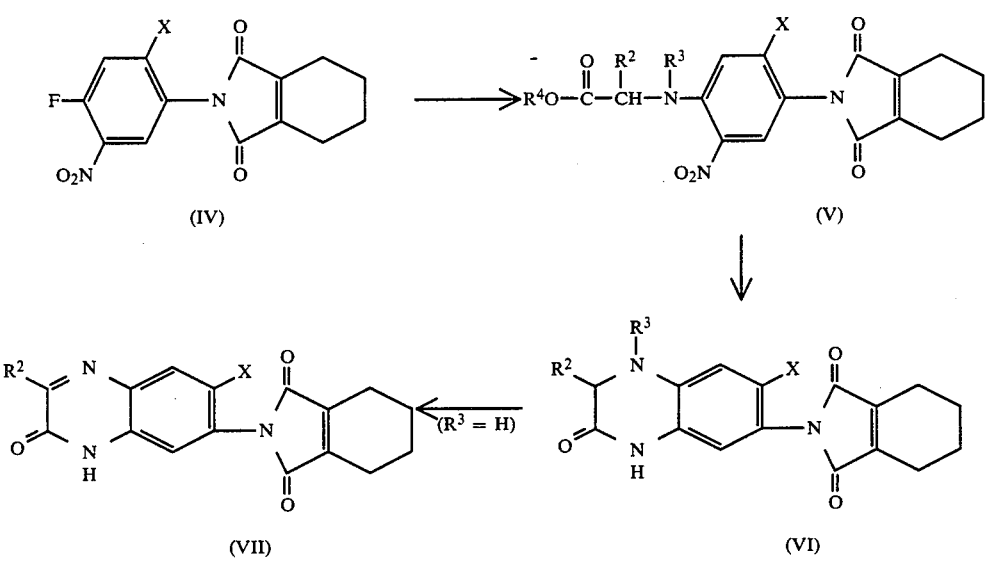

wherein X, $R^2$ and $R^3$ are each as defined above and $R^4$ is a $C_1$–$C_4$ alkyl group.

The above conversions will be explained further in detail below. Namely, the N-nitrophenylphthalimide (IV) is reacted with an amino acid ester of the formula:

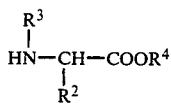

wherein $R^2$, $R^3$ and $R^4$ are each as defined above in an amount of 2.5 to 4 equivalents to one equivalent of the N-nitrophenylphthalimide (IV) in a solvent (e.g. dioxane, dimethylformamide, dimethylsulfoxide) at a temperature of 50° to 200° C. to give the N-phenylamino acid ester (V).

The resultant N-phenylamino acid ester (V) is subjected to reductive cyclization with an appropriate reducing agent, for instance, iron in an acid (e.g. acetic acid) to give the dihydroquinoxalinone (VI). More specifically, the N-phenylamino acid ester (V) is treated with 3 to 10 equivalent amounts of powdery iron such as electrolytic iron or reduced iron in a solvent (e.g. water, alcohol, acetic acid, ethyl acetate) in the existence of an excessive amount of an acid (e.g. acetic acid, hydrochloric acid) at a temperarture of 50° to 200° C.

Still, the compound (I) wherein A is

may be prepared through the quinoxalinone (VII), which is obtainable by oxidizing the dihydroquinoxalinone (VI) in an excessive amount of hydrogen peroxide in the presence of sodium hydroxide.

The quinoxaline (II) as well as the N-phenylamino acid ester (V) are novel, while the N-nitrophenylphthalimide (IV) is per se known and obtainable by the method as described in EP-A-0077938A.

Typical examples for production of the starting compounds (V) and (VI) are illustratively shown in the following Examples.

EXAMPLE 2

2-(4-Fluoro-3-nitrophenyl)-4,5,6,7-tetrahydro-2H-isoindole-1,3-dione (5.8 g) was added to a mixture of glycine methyl ester hydrochloride (7.5 g), triethylamine (6 g) and 1,4-dioxane (50 ml), and the resultant mixture was heated under reflux for 4 hours, followed by addition of water and extraction with ethyl acetate. The extract was washed with water, dried and concentrated. The residue was crystallized from methanol to give 2-(4-methoxycarbonylmethylamino-3-nitrophenyl)-4,5,6,7-tetrahydro-2H-isoindole-1,3-dione (2.6 g). m.p., 220° C.

In the same manner as above, the N-phenylamino acid esters (V) as shown in Table 2 were obtained:

TABLE 2

| Compound No. | X | $R^2$ | $R^3$ | $R^4$ | Physical constant |
|---|---|---|---|---|---|
| a | F | H | H | $CH_2CH_3$ | m.p., 166.8° C. |
| b | F | H | $CH_3$ | $CH_2CH_3$ | m.p., 159.2° C. |
| c | Cl | H | H | $CH_2CH_3$ | m.p., 153–154° C. |

EXAMPLE 3

2-(4-Methoxycarbonylmethylamino-3-nitrophenyl)-4,5,6,7-tetrahydro-2H-isoindole-1,3-dione (2.06 g) was dissolved in a mixture of acetic acid (20 ml) and ethyl acetate (20 ml), and the resultant solution was dropwise added to a mixture of 5% aqueous acetic acid (10 ml) and iron powder (4 g) at 70° to 80° C., followed by stirring at the same temperature for 3 hours. The reaction mixture was allowed to cool, diluted with water and extracted with ethyl acetate. The extract was washed with sodium bicarbonate solution, dried and concentrated to give 2-(3,4-dihydro-2(1H)-quinoxalinon-7-yl)-4,5,6,7-tetrahydro-2H-isoindole-1,3-dione (1.3 g). m.p., 208°–209° C.

In the same manner as above, the dihydroquinoxalinones (VI) as shown in Table 3 were obtained.

TABLE 3

| Compound No. | X | $R^2$ | $R^3$ | Physical constant |
|---|---|---|---|---|
| d | H | H | $CH_3$ | m.p., 263.4° C. |
| e | F | H | H | m.p., 236.6° C. |
| f | F | $CH_3$ | H | m.p., >220° C. |
| g | Cl | H | H | m.p., 174° C. |

EXAMPLE 4

2-(3,4-Dihydro-6-fluoro-2(1H)-quinoxalinon-7-yl)-4,5,6,7-tetrahydro-2H-isoindole-1,3-dione (0.43 g) was added to a mixture of sodium hydroxide (0.16 g), water (2.1 ml) and 30% aqueous hydrogen peroxide (0.21 ml), and the resultant mixture was stirred at room temperature for 16 hours. Ether was added thereto to separate an aqueous layer, which was adjusted to pH 4 with acetic acid. The precipitated crystals were collected by filtration and washed with water to give 2-(6-fluoro-2(1H)-quinoxalinon-7-yl)-4,5,6,7-tetrahydro-2H-isoindole-1,3-dione (0.32 g). m.p., >300° C.

On the practical usage of the tetrahydrophthalimides (I), they may be applied in any preparation form such as emulsifiable concentrates, wettable powders, suspensions, granules, etc. in combination with conventional solid or liquid carriers or diluents as well as surface active agents or auxiliary agents. The content of the tetrahydrophthalimides (I) as the active ingredient in such formulation form is usually within a range of 0.05 to 90% by weight, preferably of 0.1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts are by weight. The compound number of the active ingredient corresponds to the one in Table 1.

FORMULATION EXAMPLE 1

Fifty parts of Compound No. 14, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of Compound No. 8, 14 parts of polyoxyethylenestyrylphenyl ether, 6 parts of calcium dodecylbenzenesulfonate, 30 parts of xylene and 45 parts of N,N-dimethylformamide are well mixed to obtain an emulsifiable concentrate.

FORMULATION EXAMPLE 3

Two parts of Compound No. 5, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 8 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

The tetrahydrophthalimides (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the tetrahydrophthalimides (I) over the top of the plants. It may also be applied directly to the weeds if care is taken to keep the chemical off the crop foliage.

The tetrahydrophthalimides (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the tetrahydrophthalimides (I) can be used as herbicides applicable to agricultural plowed field as well as paddy field. They are also useful as herbicides to be employed for orchard, pasture land, lawn, forest, nonagricultural field, etc.

The dosage rate of the tetrahydrophthalimides (I) may vary on prevailing weather conditions, formulation used, prevailing season, mode of application, soil involved, crop and weed species, etc. Generally, however, the dosage rate is from 0.02 to 100 grams, preferably from 0.05 to 50 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the tetrahydrophthalimides (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants. The compounds shown in Table 4 below were used for comparison.

TABLE 4

| Compound No. | Chemical structure | Remarks |
|---|---|---|
| A | Cl-(ring with Cl, Cl)-O-(ring)-NO$_2$ | Commercially available herbicide; "chloronitrofen" |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designed amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 5.

TABLE 5

| Compound No. | Dosage (g/are) | Herbicidal activity | | |
|---|---|---|---|---|
| | | Japanese millet | Tall morningglory | Velvetleaf |
| 1 | 20 | 5 | 5 | 5 |
| | 10 | — | 5 | 5 |
| 2 | 20 | 5 | 5 | 5 |
| | 10 | 4 | 5 | 5 |
| 5 | 20 | 5 | 5 | 5 |
| | 10 | — | 5 | 5 |
| 8 | 20 | 5 | 5 | 5 |
| 11 | 20 | 5 | 5 | 5 |
| 14 | 20 | 5 | 5 | 5 |
| 17 | 20 | 5 | 5 | 5 |
| | 10 | 5 | 5 | 5 |
| A | 20 | 1 | 1 | 2 |
| | 10 | 0 | 0 | 0 |

TEST EXAMPLE 2

Cylindrical plastic pots (diameter, 10 cm; height, 10 cm) were filled with upland field soil, and the seeds of Japanese millet, radish and velvetleaf were sowed therein and cultivated in a greenhouse for 10 days. A designed amount of the test compound formulated in an emulsifiable concentrate according to Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined.

The results are shown in Table 6.

TABLE 6

| Compound No. | Dosage (g/are) | Herbicidal activity | | |
|---|---|---|---|---|
| | | Japanese millet | Radish | Velvetleaf |
| 1 | 5 | 4 | 5 | 5 |
| 2 | 5 | 4 | 5 | 5 |
| 3 | 5 | 5 | 5 | 5 |
| 4 | 5 | — | 5 | 5 |
| 5 | 5 | 5 | 5 | 5 |
| | 2.5 | — | 5 | 5 |
| 6 | 5 | 4 | 5 | 5 |
| 7 | 5 | 4 | 5 | 5 |
| 8 | 5 | — | 5 | 5 |
| 10 | 5 | 5 | 5 | 5 |
| 11 | 5 | 5 | 5 | 5 |
| 12 | 5 | 5 | 5 | 5 |
| 13 | 5 | 4 | 5 | 5 |
| 14 | 5 | 5 | 5 | 5 |
| | 2.5 | 4 | 5 | 5 |
| 15 | 5 | — | 5 | 5 |
| 16 | 5 | — | 5 | 5 |
| 17 | 5 | 4 | 5 | 5 |
| A | 5 | 2 | 0 | 3 |
| | 2.5 | 0 | 0 | 1 |

TEST EXAMPLE 3

Cylindrical plastic pots (diameter, 8 cm; height, 12 cm) were filled with paddy field soil, and the seeds of barnyardgrass (*Echinochloa oryzicola*) and broad-leaved weeds (e.g. common falsepimpernel, indian toothcup, waterwort) were sowed in 1 to 2 cm depth. Water was poured therein to make a flooded condition, and rice seedlings of the 2-leaf stage were transplanted therein and grown in a greenhouse. Six days (at that time the weeds began to germinate) thereafter, a designed amount of the test compound formulated in an emulsifiable concentrate according to Formulation Example 2 and diluted with water (5 ml) was applied to the pots by perfusion. The test plants were grown for further 20 days in the greenhouse, and the herbicidal activity was The results are shown in Table 7.

TABLE 7

| Compound No. | Dosage (g/are) | Herbicidal activity | | |
|---|---|---|---|---|
| | | Rice plant | Barnyardgrass | Broad-leaved weed |
| 5 | 20 | — | 5 | 5 |
| | 10 | 0 | 4 | 5 |
| 14 | 20 | — | 5 | 5 |
| | 10 | 1 | 4 | 5 |
| A | 20 | — | 5 | 5 |
| | 10 | 0 | 4 | 5 |

TEST EXAMPLE 4

Vats (33 cm × 23 cm × 11 cm) were filled with upland field soil, and the seeds of soybean, cotton, corn, common cocklebur, tall morningglory, velvetleaf, redroot pigweed, black nightshade, barnyardgrass and green foxtail were sowed therein to 1 to 2 cm depth. A designed amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 8.

TABLE 8

| Compound No. | Dosage (g/are) | Herbicidal activity | | | | | | | | |
|---|---|---|---|---|---|---|---|---|---|---|
| | | Soybean | Cotton | Corn | Common cocklebur | Tall morning-glory | Velvet-leaf | Redroot pigweed | Black night-shade | Barn-yard-grass | Green fox-tail |
| 2 | 5 | 0 | 0 | — | — | 4 | 5 | 5 | 4 | 4 | 5 |
| 5 | 5 | 1 | 1 | 0 | 4 | 4 | 5 | 5 | 5 | 5 | 5 |
| 8 | 5 | — | — | 0 | 5 | 4 | 5 | 5 | 5 | 4 | 5 |
| 10 | 5 | — | — | 0 | — | 5 | 4 | 5 | 4 | — | 4 |
| 12 | 5 | — | — | 0 | 4 | — | 4 | 4 | 4 | — | — |
| 14 | 5 | — | — | — | 5 | 5 | 5 | 5 | 5 | 5 | 5 |
| 17 | 5 | 0 | 0 | — | — | — | 5 | 5 | 5 | 5 | 5 |
| A | 5 | 0 | 0 | 0 | 0 | 0 | 1 | 1 | 1 | 1 | 0 |

TEST EXAMPLE 5

Vats (33 cm × 23 cm × 11 cm) were filled with upland field soil, and the seeds of wheat, catchweed bedstraw, persian speedwell, common chickweed, common lambsquarters, pale smartweed, wild buckwheat and annual bluegrass were sowed therein to 1 to 2 cm depth. A designed amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 27 days, and the herbicidal activity was examined.

The results are shown in Table 9.

TABLE 9

| | | Herbicidal activity | | | | | | | |
|---|---|---|---|---|---|---|---|---|---|
| Compound No. | Dosage (g/are) | Wheat | Catchweed bedstraw | Persian speedwell | Common chickweed | common lambsquarters | Pale smartweed | Wild buckwheat | Annual bluegrass |
| 5 | 2.5 | 1 | — | 5 | 5 | 5 | — | 5 | 5 |
| 8 | 2.5 | 1 | 5 | 5 | 5 | 5 | 4 | 5 | 4 |
| 10 | 2.5 | 0 | — | 5 | 5 | 5 | 5 | 5 | — |
| 14 | 1.25 | 0 | 4 | 5 | 5 | 5 | 4 | 5 | — |
| A | 2.5 | 0 | 0 | 0 | 0 | 0 | 0 | 0 | 0 |

TEST EXAMPLE 6

Vats (33 cm × 23 cm × 11 cm) were filled with upland field soil, and the seeds of corn, wheat, sugar beet, common cocklebur, velvetleaf, black nightshade, tall morningglory, common lambsquarters and green foxtail were sowed therein and cultivated for 18 days in a greenhouse. A designed amount of the test compound formulated in an emulsifiable concentrate according to Formulation Example 2 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although growing stage of the test plants varied depending on their species.

The results are shown in Table 10.

TABLE 10

| | | Herbicidal activity | | | | | | | | |
|---|---|---|---|---|---|---|---|---|---|---|
| Compound No. | Dosage (g/are) | Corn | Wheat | Sugar beet | Common cocklebur | Velvetleaf | Black nightshade | Tall morningglory | Common lambsquarters | Green foxtail |
| 1 | 0.3 | 1 | 1 | — | 5 | 5 | 5 | 4 | 5 | — |
| 3 | 0.3 | — | 1 | 3 | 4 | 4 | 4 | 5 | 5 | — |
| 5 | 0.3 | — | — | 5 | 5 | 5 | 5 | 5 | 5 | — |
|   | 0.1 | 0 | 1 | 5 | 5 | 5 | 5 | 5 | 5 | — |
| 8 | 0.3 | 1 | — | 5 | 5 | 5 | 5 | 5 | 5 | — |
|   | 0.1 | 1 | 1 | 4 | 5 | 5 | 5 | 5 | 5 | — |
| 12 | 0.3 | — | 1 | 5 | 5 | 5 | 5 | 5 | 5 | — |
| 14 | 0.3 | 1 | — | 5 | 5 | 5 | 5 | 5 | 5 | — |
|    | 0.1 | 0 | 0 | 5 | 5 | 5 | 5 | 5 | 5 | — |
| 15 | 0.3 | — | 1 | 2 | 5 | 5 | 5 | 5 | 5 | — |
| A | 0.3 | 0 | 0 | 0 | 0 | 1 | 0 | 0 | 1 | 0 |
|   | 0.1 | 0 | 0 | 0 | 0 | 0 | 0 | 0 | 0 | 0 |

What is claimed is:

1. A compound of the formula:

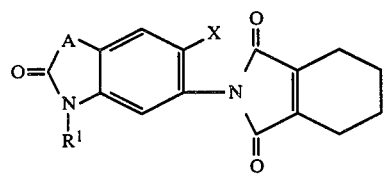

wherein $R^1$ is a $C_1$–$C_5$ alkyl group, a $C_3$–$C_5$ alkenyl group, a $C_3$–$C_5$ alkynyl group or a $C_1$–$C_3$ alkoxymethyl group, X is a hydrogen atom, a fluorine atom or a chlorine atom and A is a group of the formula:

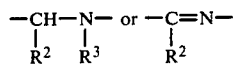

in which $R^2$ is a hydrogen atom or a methyl group, $R^3$ is a hydrogen atom or a methyl group and the nitrogen atom is bonded to the benzene ring.

2. The compound according to claim 1, wherein X is a fluorine atom.

3. The compound according to claim 1, wherein A —$CH_2$—NH— or —CH=N—.

4. The compound according to claim 1, wherein A is —$CH_2$—NH— or —CH=N— and $R^1$ is —$CH_2$C≡CH or —$CH_2$CH=$CH_2$.

5. The compound according to claim 1, which is 2-[1-(2-propenyl)-2(1H)-quinoxalinon-7-yl]-4,5,6,7-tetrahydro-2H-isoindole-1,3-dione.

6. The compound according to claim 1, which is 2-[3,4-dihydro-1-(2-propynyl)-2(1H)-quinoxalinon-7-yl]-4,5,6,7-tetrahydro-2H-isoindole-1,3-dione.

7. The compound according to claim 1, which is 2-[6-fluoro-1-(2-propenyl)-2(1H)-quinoxalinon-7-yl]-4,5,6,7-tetrahydro-2H-isoindole-1,3-dione.

8. The compound according to claim 1, which is 2-[3,4-dihydro-6-fluoro-1-(2-propynyl)-2(1H)-quinoxalinon-7-yl]-4,5,6,7-tetrahydro-2H-isoindole-1,3-dione.

9. A composition which comprises as an active ingredient a herbicidally effective amount of the compound according to claim 1, and an inert carrier or diluent.

10. A method for exterminating harmful weeds which comprises applying as an active ingredient a herbicidally effective amount of the compound according to claim to the area where the weeds grow or will grow.

11. A compound of the formula:

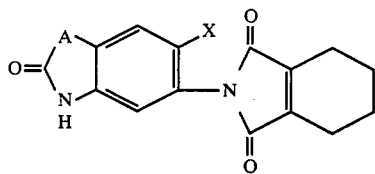

wherein X is a hydrogen atom, a fluorine atom or a chlorine atom and A is

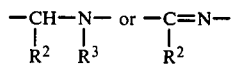

in which $R^2$ is a hydrogen atom or a methyl group, $R^3$ is a hydrogen atom or a methyl group and the nitrogen atom is bonded to the benzene ring.

12. A method for exterminating harmful weeds which comprises applying as an active ingredient a herbicidally effective amount of the compound according to claim 8 to the area where the weeds grow or will grow.

* * * * *